United States Patent [19]

Fratzer

[11] Patent Number: 4,874,603
[45] Date of Patent: Oct. 17, 1989

[54] USE OF VITAMIN E FOR NORMALIZATION OF BLOOD COAGULATION DURING THERAPY WITH HIGH UNSATURATED FATTY ACIDS OF OMEGA-3 TYPE

[76] Inventor: Uwe Fratzer, Lauberweg 29, D-6719 Hettenleidelheim, BRD, Fed. Rep. of Germany

[21] Appl. No.: 168,155

[22] Filed: Mar. 15, 1988

[30] Foreign Application Priority Data

Jun. 6, 1987 [DE] Fed. Rep. of Germany ....... 3719097

[51] Int. Cl.$^4$ .................... A61K 31/355; A61K 31/20
[52] U.S. Cl. ....................................... 424/10; 514/458; 514/560; 514/922
[58] Field of Search .................. 424/10; 514/557, 560, 514/458, 922

[56] References Cited

U.S. PATENT DOCUMENTS

| | | | |
|---|---|---|---|
| 4,211,782 | 7/1980 | Vane et al. | 514/458 |
| 4,501,582 | 2/1985 | Schulz | 206/570 |
| 4,572,915 | 2/1986 | Crooks | 514/458 |

FOREIGN PATENT DOCUMENTS

| | | |
|---|---|---|
| 59-039258 | 3/1984 | Japan . |
| 60-123414 | 2/1985 | Japan . |
| 60-192547 | 10/1985 | Japan . |
| 62-11079 | 1/1987 | Japan .................... 514/458 |

OTHER PUBLICATIONS

Puritan's Pride Catalogue, p. 67.
Chem. Abstracts 99(5):38684h, Tocopheryleicospentaenote, 8/1/83.
Chem. Abstracts 104(2):10616k, Capsules Containing Lecithins, Vitamin E and Eicosapentaenoic Acid, 1/13/86.
Chem. Abstracts 95(13):115302d, α-Tocophenyl 5, 8, 11, 14, 17 Eicosapentaenoate, 9/28/81.
R. Saynor et al., IRCS Medical Science: Biochemistry:- Cardiovascular System: Clinical Biochemistry:Clinical Pharmacology, etc., "Effect of a Marine Oil High in Elcosapentalenoic Acid on Blood Lipids and Coagulation, etc.", 8,378(1980).
Takashi Terano et al., *Atherasclerosis*, "Effect of Oral Administration of Highly Purified Eicosapentaenoic Acid on Platelet Function, Blood Viscosity and Red Cell Deformability in Healthy Human Subjects", 46(1983), pp. 321–331.
Handbook of Vitamins (1984), p. 129.
Kirk-Othmer, Concise Encyclopedia of Chemical Technology, 1985, p. 963.
Ann. Rev. Biochem., 1978 Prostaglandins and Thromboxanes, pp. 995–1029.

*Primary Examiner*—Douglas W. Robinson
*Assistant Examiner*—Raymond J. Henley II
*Attorney, Agent, or Firm*—Foley & Lardner, Schwartz, Jeffery, Schwaab, Mack, Blumenthal & Evans

[57] ABSTRACT

Blood coagulation can be normalized in persons consuming high saturated fatty acids of omega-3 type, such as eicosapentanoic acid and docosahexanoic acid, by administration of vitamin E in an amount between about 40% to 100% by weight of the fatty acid(s). An article of manufacture is thus provided comprising such fatty acids and vitamin E.

4 Claims, No Drawings

USE OF VITAMIN E FOR NORMALIZATION OF BLOOD COAGULATION DURING THERAPY WITH HIGH UNSATURATED FATTY ACIDS OF OMEGA-3 TYPE

BACKGROUND OF THE INVENTION

The present invention relates to use of vitamin E to normalize blood coagulation during the oral intake of high unsaturated fatty acids of omega-3 type ("omega-3 fatty acids") i.e., fatty acids that have a double bond between carbons 3 and 4 such as eicosa-pentanoic acid ("EPA") and docosahexanoic acid "DHA"). In the context of the present invention, "high" unsaturated fatty acids are those that comprise 3 to 6 preferably 5 to 6 double bonds and 18 to 22 preferably 20 to 22 carbon atoms.

In the 1960s and 1970s, the eating habits of Eskimos in Greenland were studied to determine if a relationship existed between the food they consumed and an observed, low rate of myocardial and brain infarctions. A relationship between consumption of fish oil and the low rate of infarctions was found to exist.

Studies of fish oil revealed that its major constituent was high unsaturated fatty acids of omega-3 type, especially EPA and DHA. Further studies revealed that upon ingestion, EPA and DHA, instead of arachidonic acid ("AA"), also known as eicosatetranoic acid, became integrated into the platelet membranes, thereby reducing platelet aggregation and changing the rheological properties of the blood in a positive way, resulting in less infarction. Coincidental with the use of such fatty acids, formation of anti-inflammatory leukotrienes, and a reduction in blood sugar levels and in increases in blood pressure were observed.

A significant finding relating to the risk of infarction is that, with continuous use of the abovementioned fatty acids in quantities of about 50-1000 mg/day, blood cholesterol levels were reduced as much as 35% and blood triglyceride levels were reduced as much as 58%. Reduction in blood cholesterol level refers, in particular, to reduction in low density lipoproteins ("LDL") and a corresponding increase in high density lipoproteins ("HDL"), which counteract infarction.

A side effect of their fish diet is an increased tendency among the Eskimos to bleed, as reported by Saynor and Varell, *Medical Science* 8: 379 (1980). These authors were unable to find in the Eskimos, however, any sigificant change in partial thromboplastin time ("PTT") or in thrombin coagulation time. In contrast, Terano et al, *Atherosclerosis*, 46: 321-331 (1983), found a significant increase in prothrombin time ("PT"), from 11.5 to 12.6 seconds, but no significant changes in PTT, cholesterol phospholipid, HDL-cholesterol, malondialdehyde and vitamin E levels in the serum of these Eskimos.

Based upon an examination of over one hundred patients given high unsaturated fatty acids such as EPA and/or DHA in quantities of up to 1000 mg/day, over a period of four or more weeks, it was found that the PT of these patients, measured as a "Quick value," dropped below that of an untreated patient, resulting in a reduction to 45% below normal.

For purposes of this description, the phrase "Quick value" is used to denote normal prothrombin time, measured with diluted plasma of healthy persons (i.e., 12 seconds), divided by a test subject's prothrombin time. Prothrombin time is measured in accordance with conventional laboratory methods. In essence, citrated plasma is mixed with a surplus of thrombokinase and calcium chloride, and time required for coagulation is measured. An increase in prothrombin time, therefore, is equivalent to a decrease in Quick value.

For patients undergoing treatment with anticoagulants such as indandiones and dicumaroles, use of high unsaturated fatty acids can intensify the effect of anticoagulants, and can lead to a fast drop in Quick value to beyond a therapeutically safe limit, necessitating discontinuation of anticoagulants. Omega-3 fatty acids are used not only under direct medical supervision in the treatment of acute illnesses but also prophylactically by the lay public, without medical supervision, as dietetic supplements. Accordingly, the above-described risk is considerable.

Consequently, it would be desirable if there is some way in which blood coagulation, measured as PT, can be normalized despite a person's use or consumption of a high dose of high unsaturated fatty acids like EPA and DHA.

SUMMARY OF THE INVENTION

It is therefore an object of the present invention to counteract the effect of an increased tendency to bleed caused by consumption of high unsaturated fatty acids such as eicosapentanoic acid and docosahexanoic acid.

It is another object of the present invention to counteract the aforementioned effect without adversely influencing the ability of such fatty acids to cause a reduction in blood cholesterol level.

It is yet another object of the present invention to provide a means to normalize blood coagulation in persons who consume high unsaturated fatty acids.

In accomplishing these and other objects, there has been provided, in accordance with one aspect of the present invention, a method for normalization of blood coagulation during intake of a high omega-3 fatty acid, comprising the step of combining oral administration of a predetermined amount of said fatty acid with oral administration of vitamin E, wherein said vitamin E is administered in an amount ranging from about 40 to 100% by weight of said amount of fatty acid.

In accordance with another aspect of the present invention, an article of manufacture comprising vitamin E and at least one omega-3 fatty acid wherein said vitamin E is present in an amount ranging from about 40% to 100% by weight of said fatty acid. In one preferred embodiment, the article of manufacture comprises a kit, in which vitamin E and the omega-3 fatty acid are kept in separate containers. In another preferred embodiment, the article of manufacture comprises a mixture of omega-3 fatty acid and vitamin E.

Further objects, features and advantages of the present invention will become apparent from the following detailed description. It should be understood, however, that the detailed description and specific example, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The present invention relates to the use of vitamin E for normalization of blood coagulation during intake of omega-3 fatty acid, such as EPA and DHA, wherein the amount of vitamin E used is 40 to 100% by weight of the fatty acids.

The present invention also relates to an article of manufacture, either in the form of a kit or a mixture comprising omega-3 fatty acid and vitamin E, the latter of which is 40 to 100% by weight of the fatty acids.

It has been discovered that vitamin E, also known as alpha-tocopherolacetate, when used in combination with omega-3 fatty acid, at a concentration of about 40 to 100% by weight relative to the weight of said fatty acid, effectively prevents an increase in prothrombin time or restores to normalcy, within a short time, an existing increase in prothrombin time.

In accordance with the present invention, omega-3 fatty acids like EPA and DHA can be used as a fish oil preparation, as a concentrate, or in a purified form, all in the form of a liquid or a capsule. Such an omega-3 fatty acid can be administered as a drug or taken as a dietary supplement in a dose sufficient to cause an increase in prothrombin time, preferably, in an amount ranging from 50 to 1000 mg per dose.

Pursuant to the present invention, vitamin E can be taken separately, e.g., in the form of a commercially available preparation like tocopherolacetate, or in admixture with an omega-3 fatty acid. The amount of vitamin E to be taken, within the context of the present invention, depends on the amount of omega-3 fatty acid to be used. Doses of vitamin E sufficient to cause normalization of prothrombin time can be taken, with the amount preferably ranging from about 40% to 100% by weight of the amount of fatty acid taken (or to be taken), and most preferably, in an amount ranging from about 30 to 1000 mg per dose.

Doses of vitamin E higher than the abovedescribed range generally produce no additional effect and are preferably not used, thereby to avoid increasing the dosage and the risk of incurring undesirable side effects unnecessarily, and to avoid economic waste. Doses of vitamin E lower than the above-described range are typically ineffective, particularly in the range of 1% to 3% by weight of omega-3 fatty acid, for example, when used in the 1% to 2% range as an antioxidant in mixtures comprising fatty acid, which is relatively oxidation-sensitive.

Appropriate doses of vitamin E can be taken in parallel with the fatty acids, or taken separately, e.g., after commencement of omega-3 fatty acid therapy. In accordance with the present invention, an article of manufacture can be prepared that comprises omega-3 fatty acid and vitamin E as separate components in a kit, or that comprises omega-3 fatty acid in admixture with vitamin E.

The vitamin E suitable for use in the present invention includes preparations in soft or hard gelatin capsules, preparations in the form of tablets, or sugar-coated tablets, and preparations mixed into fish oil.

Vitamin E and the omega-3 fatty acid preparations can optionally comprise other auxiliary substances of the sort usually present in commercial preparations of these compounds. One preferred embodiment of the present invention comprises a mixture of high unsaturated fatty acids such as EPA and/or DHA, in an amount of about 50 to 1000 mg and vitamin E, in an amount of about 40 to 1000 mg, in a single dose. This mixture can be given orally every day over a period of time to treat patients who are in a high risk group for myocardial or brain infarction, or who have a need to lower their blood cholesterol levels.

Treatment comprising such a mixture can be given, for example, for a period of 4 to 6 weeks or until the desired level of blood cholesterol is achieved or maintained.

The mechanism is unknown by which vitamin E maintains or restores normal blood coagulation when used at a high concentration in combination with high unsaturated fatty acids. Perhaps the spontaneous drop in Quick value upon fatty acid consumption is caused by a decrease in prothrombin formation resulting from bonding of vitamin K to the high unsaturated fatty acids. Additional intake of vitamin E would then restore the level of free vitamin K, thereby restoring prothrombin formation. This explanation can account for the observation that an amount of vitamin E as a percent of an amount of unsaturated fatty acids has to be used.

In any event, the observed effect of vitamin E intake on coagulation time of patients who are ingesting omega-3 fatty acid is surprising in part because vitamin K, not vitamin E, is essential for blood coagulation. The correlation between vitamin E and coagulation time is especially unexpected since no change in serum vitamin E level has been observed during long-term usage of EPA and DHA. See Terano et al, loc. cit.

The present invention is further described below by reference to the following illustrative example.

EXAMPLE 1

Effect of vitamin E on prothrombin time of subjects given oral dosages of omega-3 fatty acids A total of one hundred and twelve (112) subjects were studied and their prothrombin times and serum vitamin E levels monitored, before and after oral administration of omega-3 fatty acid and vitamin E. Results are recorded in Table 1 below.

Fatty acids were given in the form of a capsule as either purified EPA or purified DHA, at a dose of up to 1000 mg per subject per day for a period of either six weeks (see column III) or ten weeks (see column IV), respectively. Vitamin E was given separately in a dose of 500 mg per patient per day for a period of four weeks, commencing six weeks after initiation of (but continuing administration of) fatty acid therapy (see column IV).

Prothrombin time of normal individual was determined to be approximately 12 seconds. Prothrombin time was measured, and the Quick value was calculated, for each subject, before and after treatment. The Quick values for all subjects were averaged before treatment (row 2, column II), after six weeks of treatment with omega-3 fatty acid alone (row 2, column III), and after combined treatment with omega-3 fatty acid and vitamin E (row 2, column IV).

Serum vitamin E level of each subject was determined before commencement of the omega-3 fatty acid treatment, and was found to range from about 0.5 to 1.6 mg/100 ml. Each subject's pretreatment serum vitamin E level was deemed his personal "normal value" (row 3, column II). Serum vitamin E levels, as a percentage of each subject's pretreatment level, were determined and the levels for all subjects were averaged after six week of treatment with omega-3 fatty acid alone (row 3, column III) and after combined treatment with omega-3 fatty acid and vitamin E (row 3, column IV).

TABLE 1

| | EXPERIMENTAL RESULTS | | |
|---|---|---|---|
| I | II | III | IV |
| Number of Subjects n = 112 | Before Omega-3-fatty acid therapy | After 6 Weeks of Omega-3-fatty acid therapy[1] | After 6 weeks of Omega-3-fatty acid therapy followed by 4 weeks of Omega-3 fatty acid and vitamin E therapy[2] |
| Quick value[3] | 96% n = 112 | 58% n = 112 | 95% n = 112 |
| Vitamin E (Tocopherol) | personal "normal value"[4] = 100% n = 112 | 60% of "normal value" n = 112 | 100% of "normal range" n = 112 |

LEGEND:
[1] With up to 1000 mg of EPA or DHA per dose.
[2] With EPA or DHA as in column III, and 500 mg of vitamin E per dose.
[3] Quick value = [normal prothrombin time] ÷ [prothrombin time of tested subject]. A prothrombin time of 12 seconds is used as normal prothrombin time. Results represent an average Quick value of all tested subjects expressed as a percentage of normal quick value.
[4] Normal serum vitamin E level of tested subjects ranges from about 0.5–1.6 mg/100 ml. Each subject's serum vitamin E level before treatment is his or her personal "normal value." Results represent an average of all tested subjects expressed as a percentage of his or her personal normal value.

Before administration of omega-3 fatty acid, Quick value of the 112 subjects averaged 96% of normal. After 6 weeks of omega-3 type fatty acid therapy, Quick value of these subjects dropped to an average of 58% of normal. But after 6 weeks of omega-3 type fatty acid therapy alone and 4 weeks of combined omega-3 type fatty acid therapy and vitamin E therapy, the Quick value of these subjects returned to an average of 95% of normal.

The vitamin E level was found to drop to 60% of normal when the omega-3 fatty acid was given without vitamin E, but returned to 100% of normal when fatty acid was given in combination with vitamin E.

The results show, therefore, that administration of omega-3 fatty acid lowers the Quick value of treated subjects, while administration of vitamin E restores the Quick value of treated subjects to normalcy. These results are entirely unexpected since Saynor et al, loc. cit., did not find any significant change associated with prothrombin within a 5-week period during which each tested persons was given, on a daily basis, fish oil comprising a high EPA content. In addition, Terano, loc. cit., did not find any significant changes in serum vitamin E levels in people on fish diets.

What is claimed is:

1. A method for normalization of blood coagulation during intake of a high omega-3 fatty acid, by increasing prothrombin time in a person taking said fatty acid, comprising the step of combining oral administration to said person of said fatty acid with oral administration of vitamin E to said person, wherein said vitamin E is administered in an amount ranging from about 40% to 100% by weight of said amount of fatty acid.

2. A method of normalization of blood coagulation as claimed in claim 1, wherein said fatty acid is selected from the group consisting of eicosapentanoic acid and docosahexanoic acid.

3. A method of normalization of blood coagulation as claimed in claim 1, wherein vitamin E and said fatty acid are administered at the same time.

4. A method of normalization of blood coagulation as claimed in claim 1, wherein vitamin E is administered after commencement of administration of said fatty acid.

* * * * *